United States Patent [19]

Radke et al.

[11] Patent Number: 5,413,116
[45] Date of Patent: May 9, 1995

[54] METHOD AND APPARATUS FOR DIAGNOSING JOINTS

[75] Inventors: John C. Radke, Whitefish Bay; Gregory J. Ryan, Milwaukee, both of Wis.; Troy W. Hershberger, Warsaw, Ind.

[73] Assignee: BioResearch, Milwaukee, Wis.

[21] Appl. No.: 83,219

[22] Filed: Jun. 24, 1993

[51] Int. Cl.⁶ .............................................. A61B 5/103
[52] U.S. Cl. ...................................... 128/777; 128/779
[58] Field of Search ................. 128/630, 715, 773, 782

[56] References Cited

U.S. PATENT DOCUMENTS

| | | | |
|---|---|---|---|
| 3,181,528 | 2/1961 | Brackin. | |
| 4,428,381 | 1/1984 | Hepp | 128/715 |
| 4,437,473 | 3/1984 | Mollan | 128/773 |
| 4,543,957 | 10/1985 | Friedman et al. | 128/630 |
| 4,792,145 | 12/1988 | Eisenberg et al. | 128/715 |
| 4,823,807 | 4/1989 | Russell et al. | 128/773 |
| 4,836,218 | 6/1989 | Gay et al. | 128/773 |
| 4,922,925 | 5/1990 | Crandall et al. | 128/782 |
| 5,002,065 | 3/1991 | LaCourse et al. | 128/739 |
| 5,165,417 | 11/1992 | Murphy, Jr. | 128/716 |

OTHER PUBLICATIONS

Kernohan, W. George, et al., "Vibration arthrometry—A preview," *Acta Orthop Scand,* 1990.
Christensen, L. V. and Orloff, J., "Reproducibility of temporomadibular joint vibrations," *Journal of Oral Rehabilitation,* 1992, vol. 19.
Ishigaki, Shoichi, et al., The Distribution of Internal Derangement in Patients With Temporomandibular Joint Dysfunction—Prevalence, Diagnosis, and Treatments, *The Journal of Craniomandibular Practice,* Oct. 1992.
Lippmann, Richard P., "An Introduction to Computing with Neural Nets," *IEEE ASSP Magazine,* Apr. 1987.
Kernohan, W. George, et al., "Vibration Arthrometry in Congenital Dislocation of the Hip," *Clinical Orthopaedics and Related Research,* 1989.
Chu, Mamerto L., "An Electro-Acoustical Technique for the Detection of Knee Joint Noise," *Medical Research Engineering,* 1976.
Kernohan, W. G., "Vibration arthrometry in assessment of knee disorders: the problem of angular velocity," *Scientific and Technical Record,* 1991.
Kernohan, W. George, "Four channel analogue to digital conversion for analysis of knee 'clicks'", *Physica Medica,* 1990.
Radke, J. and Christensen, L., "Artificial Neural Network Classifies TMJ Disk/Condyle Relation from Vibrations," *Journal of Dental Research,* 1992, vol. 72, p. 679.

*Primary Examiner*—Max Hindenburg
*Attorney, Agent, or Firm*—Harness, Dickey & Pierce

[57] ABSTRACT

A method and apparatus for diagnosing joints based on sensed joint vibrations. Accelerometers disposed on the skin adjacent to the joint detect vibrational patterns during movement of the joint. These patterns are then processed by one processor to generate a predetermined set of data parameters descriptive of the vibration pattern. Also, the position and velocity of the joint during the vibration is recorded. This information from numerous patients with known joint conditions is used to train a adaptive interpreter, such as a neural network, to produce an output in response to these inputs which is indicative of the known joint condition. Once trained, the adaptive interpreter can then interpret this set of parameters for an unknown joint to generate a fast and reliable diagnosis. The result is a non-subjective joint disorder classification system that can be utilized by persons without particular expertise in analyzing joint vibrational patterns.

28 Claims, 14 Drawing Sheets

CONDYLAR VIBRATION

| VIBRATION | DISTANCE FROM CO | | INTEGRAL | | MEDIAN FREQ Hz | | PEAK FREQ Hz | | PEAK AMPLITUDE | |
|---|---|---|---|---|---|---|---|---|---|---|
| | SLANT VERT | LAT | LEFT | RIGHT | LEFT | RIGHT | LEFT | RIGHT | LEFT | RIGHT |
| #1 | 31.0 | 6.4 R | 21.5 | 75.5 | 199 | 264 | 109 | 68 | 1.1 | 2.7 |
| #2 | 33.3 | 6.1 R | 41.5 | 165.5 | 179 | 212 | 43 | 127 | 2.0 | 5.6 |
| #3 | 32.2 | 6.6 R | 35.8 | 138.0 | 184 | 258 | 38 | 132 | 1.6 | 4.7 |
| #4 | 34.2 | 6.6 R | 37.5 | 140.5 | 215 | 238 | 48 | 143 | 1.5 | 4.6 |
| AVERAGE | 32.6 | 6.4 R | 32.5 | 128.2 | 189 | 238 | 48 | 132 | 1.3 | 4.0 |

| VIBRATION | INTEGRAL <300 Hz | | INTEGRAL >300 Hz | | >300 / <300 RATIO | |
|---|---|---|---|---|---|---|
| | LEFT | RIGHT | LEFT | RIGHT | LEFT | RIGHT |
| #1 | 17.0 | 41.0 | 4.5 | 34.5 | 0.26 | 0.84 |
| #2 | 33.5 | 107.5 | 8.0 | 58.0 | 0.24 | 0.54 |
| #3 | 25.3 | 79.2 | 10.5 | 58.8 | 0.42 | 0.74 |
| #4 | 24.5 | 85.2 | 13.0 | 55.3 | 0.53 | 0.65 |
| AVERAGE | 25.3 | 78.3 | 7.3 | 50.0 | 0.29 | 0.64 |

FIG. 11

|  | LEFT CONF. | RIGHT CONF. |
|---|---|---|
| NORMAL / QUIET | —— | —— |
| DISK MOVEMENT | .36 | —— |
| EMINENCE CLICK | —— | —— |
| DISP. DISK W/REDCT | —— | —— |
|    WITH DJD | —— | —— |
| DISPLACED DISK W/O REDUCTION | | |
|    QUIET | —— | —— |
|    W/VIBRATION | —— | .23 |
|    WITH DJD | —— | —— |
| DEGENERATIVE JOINT DISEASE | | |
|    EARLY | .85 | —— |
|    ADVANCED | —— | .95 |

FIG. 14

METHOD AND APPARATUS FOR DIAGNOSING JOINTS

BACKGROUND OF THE INVENTION

1. Technical Field

This invention relates to a system and method for diagnosing joint conditions, and more particularly to a system and method for automatically analyzing vibrations from moving joints to classify joint conditions.

2. Discussion

The effective treatment of joint disease depends on an accurate diagnosis. Usually the most accurate diagnostic tool is direct viewing of the joint using invasive surgical techniques. Unfortunately, the risks and costs associated with surgical diagnostic techniques are prohibitive for all but the most serious categories of conditions. For example, arthroscopy of the knee typically costs between $5,000.00 and $7,000.00.

A second choice in joint diagnosis is the use of radiological imaging techniques. These include x-rays and Computed Tonography (CT) scans, magnetic resonance imaging (MRI) and ultrasound. These techniques are used with varying degrees of success. CT scans and MRI are relatively expensive (about $500–$1,500.00) and sometimes do not reveal adequate information about the condition of the joint to permit an accurate diagnosis. In brief, neither surgery nor imaging techniques offer an ideal joint diagnostic tool for many joint disorders.

A third technique for diagnosing joints relies on the interpretation of vibrations emitted by joints. In general, the term "auscultation" is used to describe any method of examination of the functions and conditions of the human body by the sounds or vibrations they produce. Physicians have listened to sounds and felt vibrations from human joints in diagnosing joint pathology for centuries. Unfortunately, this approach has often proved to be frequently inaccurate. This is primarily due to the subjective nature of the use of hands and ears as vibration sensors. Another difficulty has been the limitations of language in communicating the types of sounds generated from joints associated with particular joint diseases from one practitioner to another. Also, auscultation depends upon the widely varying expertise of the examiner. Thus, while the characterization of joint conditions by analyzing the sounds produced by the joint shows promise as a diagnostic tool, a more objective approach than simply listening to the sounds is required to achieve the desired levels of reliability.

To overcome the shortcomings of auscultation, techniques for electronically recording joint vibrations or sounds have been developed. Once recorded, a visual display of the sounds can be generated to provide a more objective means for comparing the sounds from a patient's joint with those of joints having known pathologies. The first attempts to record joint sounds utilized microphones attached to the skin adjacent the joint. One problem with the use of microphones has been the difficulty in distinguishing articular sounds from extrinsic sounds, such as snapping tendons, noise due to hand tremors, skin friction and common background noise. This is because microphones integrate sound arising from a region of space, lacking a focus point, and precise vibration measurement at a point. Also some low frequency joint vibrations are below the dynamic range of microphones and could not therefore be detected.

For these reasons, accelerometers (or velocity transducers) have replaced microphones as the preferred sensors for recording joint sounds. This is because accelerometers have the mechanical advantage of being able to detect the direct transmission of vibrations. An accelerometer consists of a case within which is a piezoelectric crystal that has a mass resting on it. This crystal reacts to acceleration by producing a minute electric charge between its top and bottom surfaces, due to the compression produced by the mass, which is directly proportional to the acceleration. As a result, accelerometers detect only localized vibration and are sensitive to activity of very small amplitude.

The accelerometer is the basis of the new technique for joint diagnosis called vibration arthrometry. With vibration arthrometry reliable recordings of joint sounds and vibrations can be recorded and displayed. Accurate diagnosis can often be accomplished by comparing the vibrations from a patient's joint with those previously recorded from joints having particular known conditions. Nevertheless, subjective visual evaluation of the vibration waveform is still required to classify the vibration patterns. Also, the visual recognition of patterns is sometimes anecdotal; a perceived waveform may be only coincidentally related to a specific condition.

To assist in visual analysis, various statistical techniques have been employed. These include multiregression analysis, autocorrelation, and fast fourier transform analysis. These techniques are used to find parameters (for example, related to frequency and amplitude) that assist in the classification of joint conditions by their vibration patterns. However, even these statistical techniques ultimately require human interpretation to arrive at an accurate classification and diagnosis of joint condition. Moreover, a relatively high level of expertise is usually required to accurately interpret the results, limiting the usefulness of these techniques for most clinicians.

Thus, it would be desirable to provide a diagnostic tool for classifying joint conditions which is non-invasive, inexpensive and easy to use. Further, it would be desirable to provide a joint diagnostic tool having these characteristics which utilizes joint vibrations to arrive at a non-subjective joint disorder classification. Also, it would be desirable to provide technique for classifying joint conditions by the vibration patterns that can be utilized by persons without particular expertise in analyzing the joint vibrational patterns where the results do not depend upon the skill of the person conducting the test.

SUMMARY OF THE INVENTION

Pursuant to the present invention a method and apparatus for diagnosing joints is provided. In accordance with a first aspect of the present invention, a system for classifying degenerative joint disease conditions includes one or more sensors for detecting a vibration pattern from the joint. A preprocessor is provided which generates a predetermined set of data parameters descriptive of the vibration pattern. An adaptive interpreter receives these data parameters as input and produces an output which indicates at least one classification of the degenerative Joint disease condition.

In accordance with another aspect of the present invention a system for classifying trauma induced joint conditions is provided. This system includes a sensor means for detecting a vibration pattern from the joint.

Also, a preprocessor is provided for determining a set of data parameters which are descriptive of the vibration pattern. An adaptive interpreter receives the data parameters as input and produces an output which indicates at least one classification of the trauma induced condition of the joint.

In accordance with a third aspect of the present invention a system for diagnosing conditions of an implantable orthopedic device is provide which includes a sensor for detecting a vibration pattern from the implantable device. A preprocessor is provided for producing a predetermined set of data parameters descriptive of the vibration pattern. An interpreter receives the data parameters as input and provides an output which indicates at least one implantable orthopedic device condition.

In accordance with a fourth aspect of the present invention a system for classifying joint conditions in a load bearing joint is provided. The system includes sensor means for detecting a vibration pattern from the joint. Also, a pre-processor is provided for determining a set of data parameters which are descriptive of the vibration pattern. An adaptive interpreter receives the data parameters as input and produces an output which indicates at least one classification of the condition of the load bearing joint.

In the preferred embodiment, the adaptive interpreter is a neural network which has been pretrained using vibrational patterns from joints having known conditions. Once trained the neural network recognizes and classifies unknown joint conditions. The result is a non-invasive objective and reliable technique for joint diagnosis. The present invention can be utilized to quickly and inexpensively provide accurate joint condition diagnosis. Furthermore, the present invention does not require a high level of skill by the practitioner utilizing it. In particular, it does not require the subjective interpretation of vibrational patterns by an expert.

BRIEF DESCRIPTION OF THE DRAWINGS

The various advantages of the present invention will become apparent to one skilled in the art by reading the following specification and by reference to the following drawings in which:

FIG. 11 is a display of the data parameters produced by the preprocessor in FIG. 5.

FIG. 14 is a diagram of the output classification produced by the joint diagnostic system shown in FIG. 5.

DETAILED DESCRIPTION OF THE PREFERRED EMBODIMENTS

The present invention is a method and apparatus for diagnosing joints based on sensed vibrational patterns occurring during movements. This invention is particularly adapted to classifying conditions resulting from degenerative joint disease, as well as from traumatic injury. Also, the present invention can be used to detect and classify conditions existing in load bearing joints and in implantable orthopedic devices. However, as will be evident from the discussion below, the present invention may be easily adapted to the classification of other joint conditions.

Figure 1:
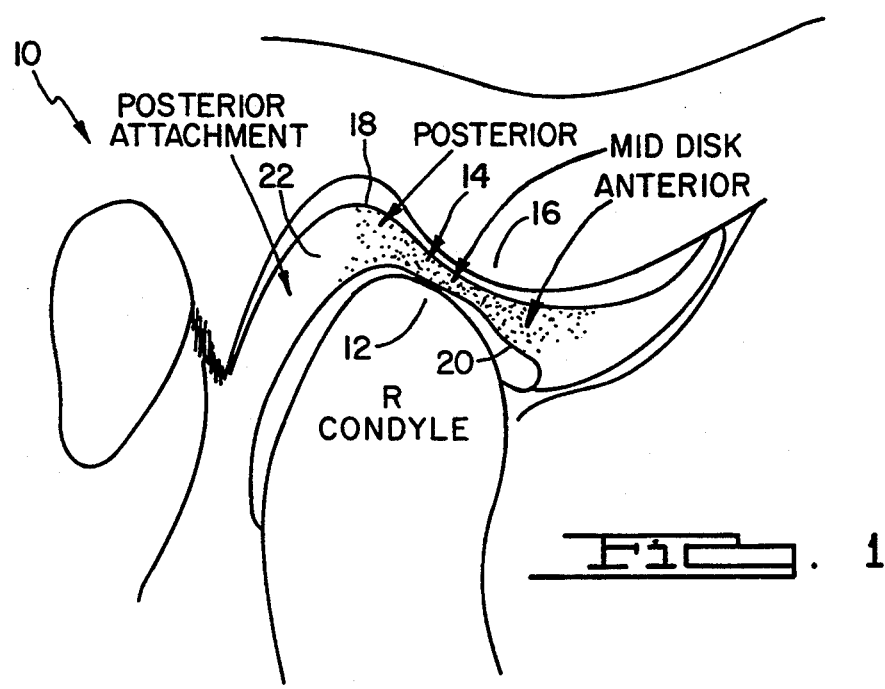
FIG. 1 is a diagram of the various components of a temporomandibular joint.

In a preferred embodiment of the present invention the diagnostic system is adapted to classify degenerate joint disease and other conditions involving the temporomandibular (TM) joint. To better understand the various conditions and disorders of the TM joint there is shown in FIG. 1 a sketch of the main components of the TM joint. The TM joint 10 comprises a condyle 12, a disc 14 and an eminence 16. The condyle is part of the mandible (jaw) and the eminence is part of the cranium. The disc has a posterior region 18 and an interior region 20. The disc is attached posteriorly to the cranium by a posterior attachment 22. Also, there are medial and lateral ligaments attaching the disc to the condyle 12 which are not shown in FIG. 1. Additional ligaments which are not shown are attached to the eminence 16 to limit the range of motion of the condyle.

Figure 2:
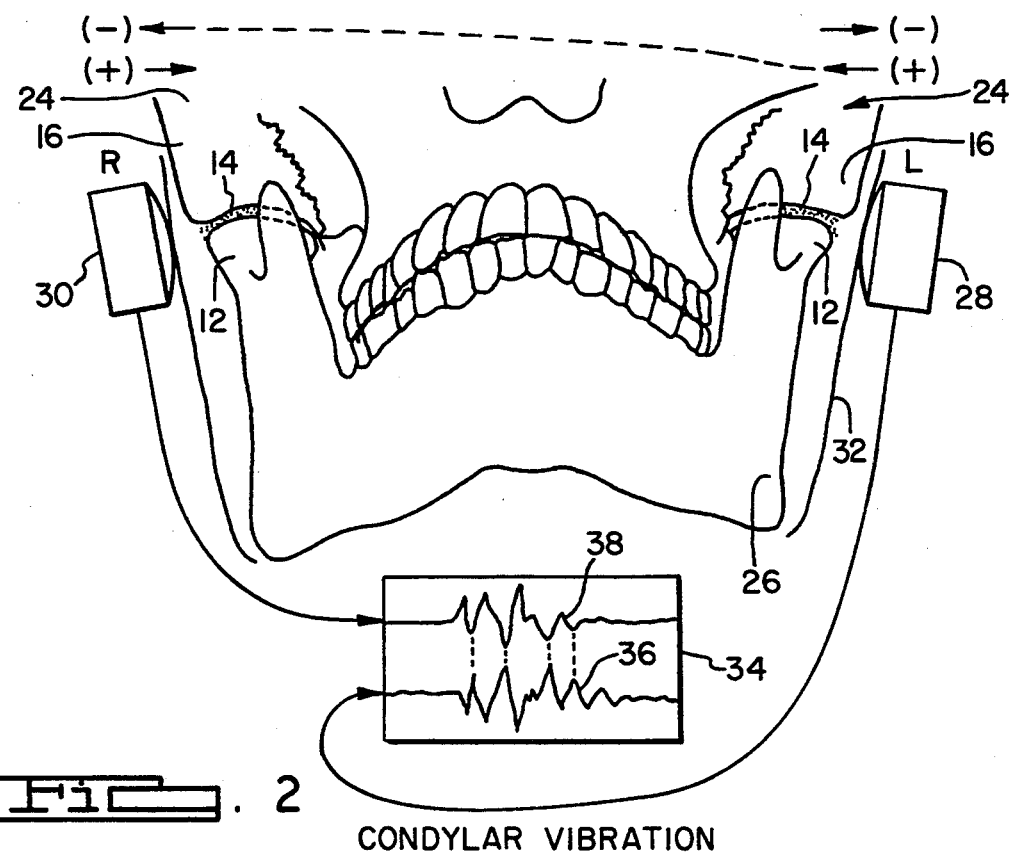
FIG. 2 is a diagram of a-technique for measuring and displaying vibrations from the temporomandibular joint in accordance with the prior art.

Referring now to FIG. 2 there is shown a larger view of the cranium 24, and mandible 26, part of which includes the left and right condyle 12. The disc 14 is shown in the space between the eminence 16 and condyle 12.

During movement of the TM joint a wide variety of vibrations may be produced, particularly where there is a TM joint disorder present. As shown in FIG. 2 in accordance with the prior art these vibrations can be detected by placing left and right sensors 28 and 30 in contact with skin 32 adjacent to the TM joint 10. Sensors 28 and 30 may comprise, for example, microphones, or accelerometers, which are preferred over microphones for the reasons discussed above. The signals received by the sensors 28 and 30 are converted into electrical signals which may be displayed in a variety of display modes as illustrated in the display 34 which shows the vibration pattern from the left 36 and right 38 TM joints respectively. Also, FIG. 2 illustrates the direction of vibration for each TM joint. Positive vibration signals are defined as vibrations in the direction toward the opposite TM joint.

Figure 3:
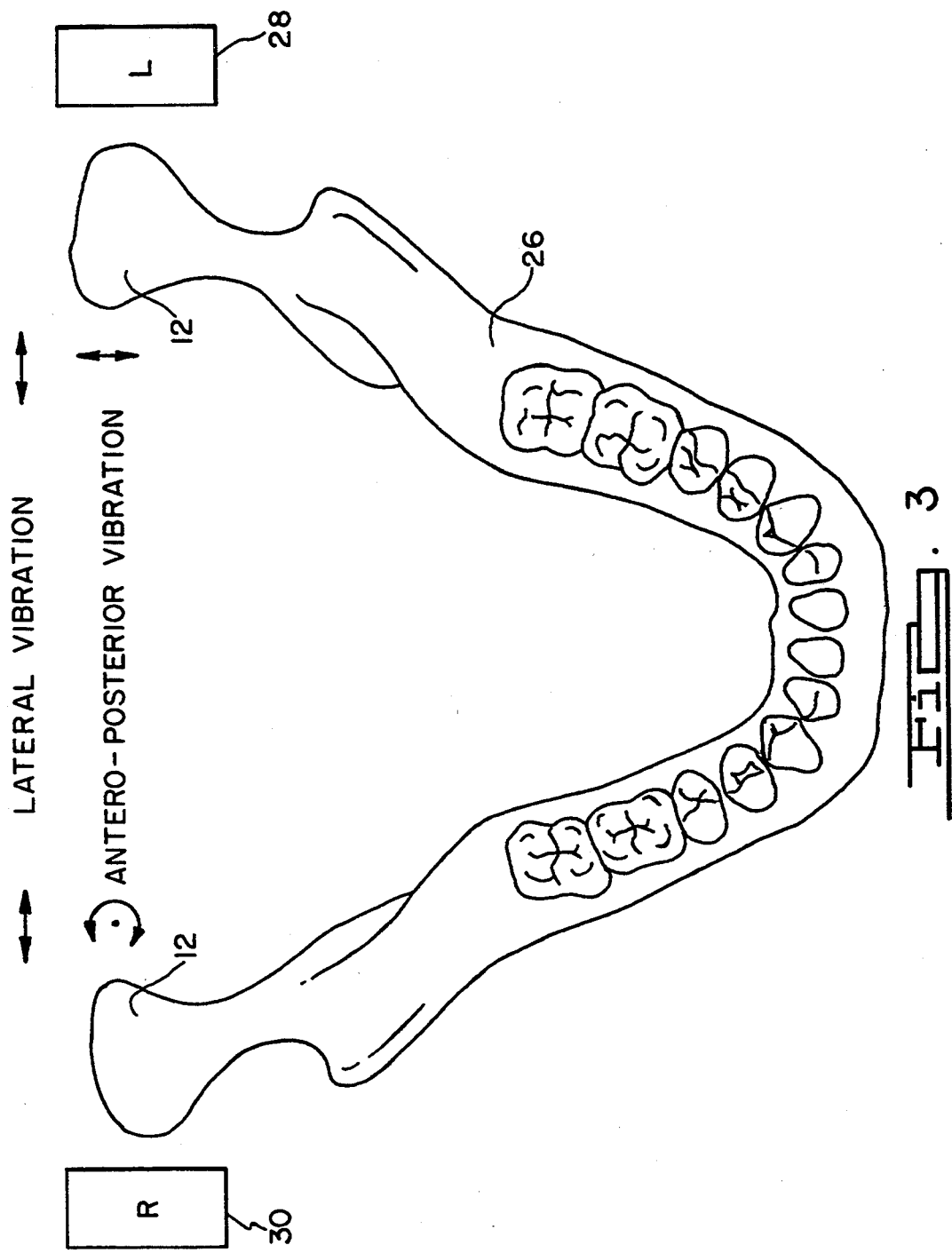
FIG. 3 is a diagram of a portion of a temporomandibular joint indicating the direction of sensed vibrations.

Referring now to FIG. 3 the mandible 26 and condyle 12 are shown in more detail, along with the left and right sensors 28 and 30. An important consideration in analyzing TMJ vibrations is the vibration direction. As shown in FIG. 3, when lateral vibrations of one condyle occur, the opposite side condyle also vibrates, but 180° out of phase. When one condyle vibrates in a vertical (up-down) or antero-posterior (forward-back) direction, little or no vibration occurs on the opposite side. Identifying the existence of a lateral vibration is part of the pre-processing of the system, as described in more detail below. This avoids the common clinical problem of diagnosing/attributing a "condition" to the wrong joint.

Figure 4A:
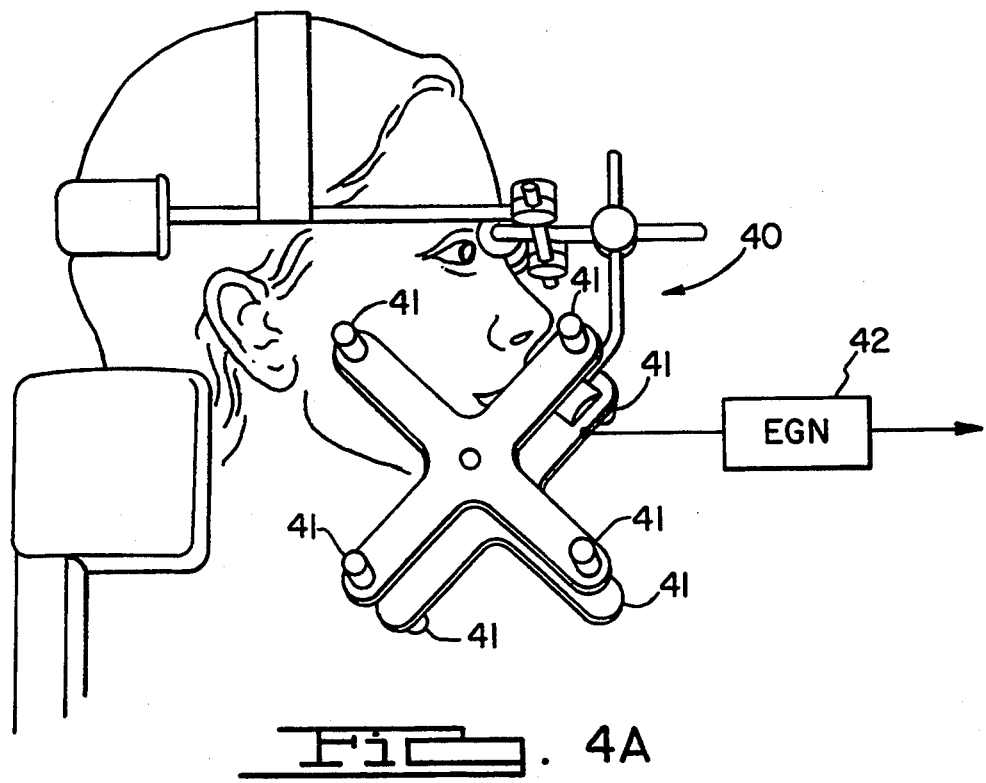
FIGS. 4A-B are diagrams of an apparatus employed to track jaw motion during measurements of temporomandibular joint (TMJ) vibrations.
Figure 4B:
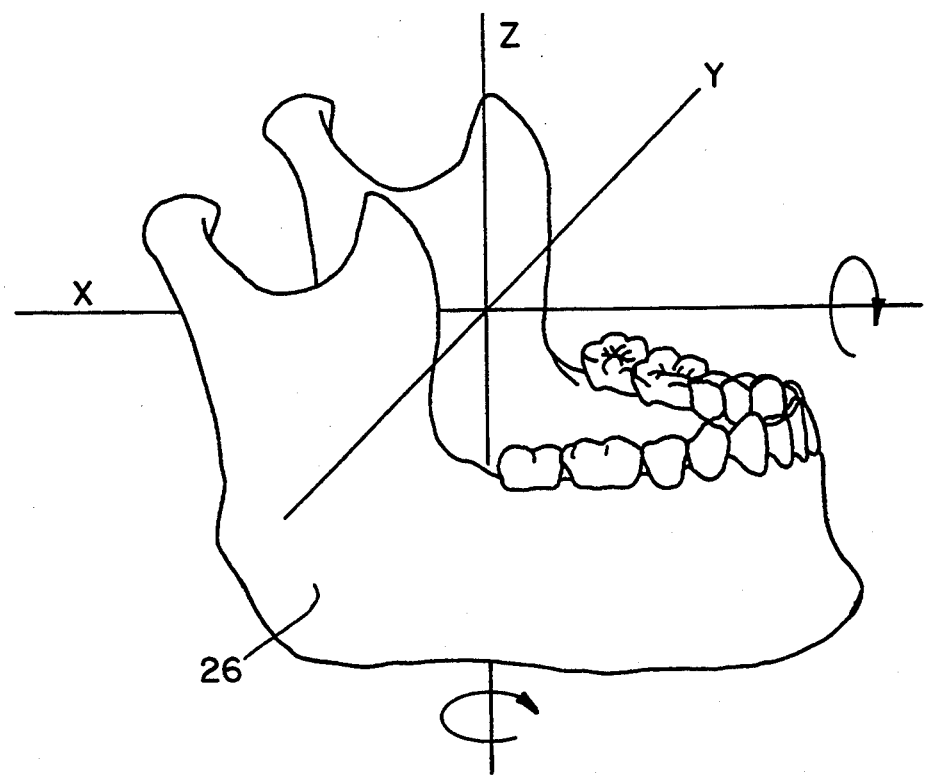

Another consideration that will be important to the analysis of TM joint vibrations will be the recording of the motion and position of the jaw during the (occurrence) of the vibration. Referring now to FIGS. 4A-B there is shown a jaw tracker 40 which the subject wears during vibration measurements in accordance with the present invention. FIG. 4B shows the directions of motion which the jaw tracker 40 measures. That is, the jaw tracker measures translation in the x, y and z directions as well as two rotations; about the x axis and about the z axis. In more detail, the jaw tracker 40 includes a small magnet (not shown) attached to the labial vestibule which is in front of the lower anterior teeth. This magnet is tracked by the tracker 40. The measurements represent the amount of movement of the lower anterior teeth. Thus, if the mandible 26 goes to the left or to the right from a starting point this distance is measured by the jaw tracker 40. In general the jaw tracker 40 measures the movement of the magnet by detecting the changes in the magnetic flux levels at 8 sensors 41 and converting them into translations/rotations of the magnet. The signals from the jaw tracker are processed in a circuit 42 referred to as a bioelectrognathograph (EGN).

Figure 5:
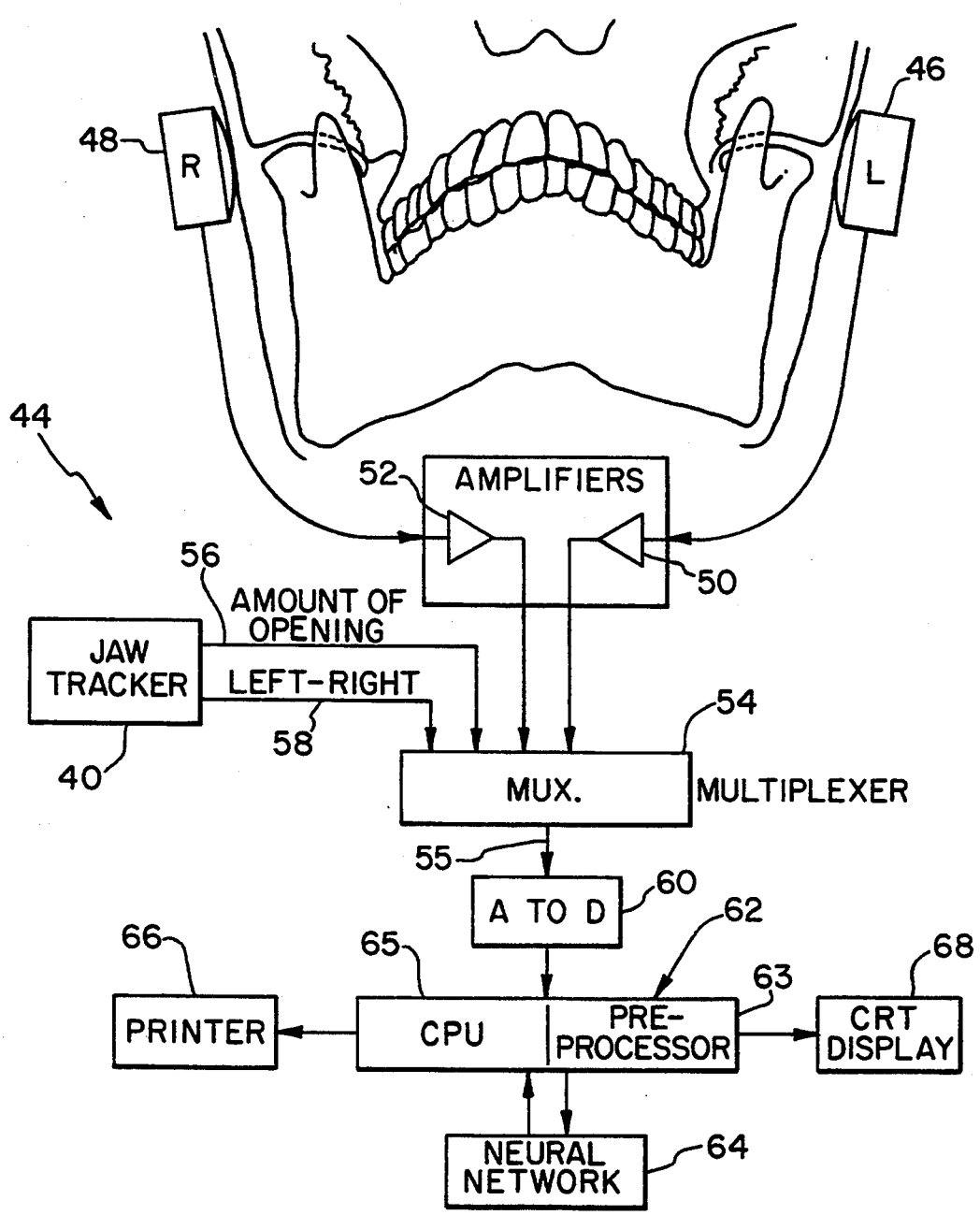
FIG. 5 is a system diagram of the main components of a preferred embodiment of the present invention employed to classify vibrational patterns from temporomandibular joints.

Referring now to FIG. 5 an overall schematic block diagram of the joint diagnostic system 44 in accordance with the present invention is shown. The system includes left and right accelerometers 46 and 48, each connected to an amplifier 50 and 52 which amplify the accelerometer's signals. These amplified signals are then transmitted to a multiplexer unit 54. Also, the jaw tracker 40 which includes the electrognathograph circuit 42 transmits a pair of signals to the multiplexer 54. The first of these signals 56 indicates the amount of opening of the jaw; and the second signal 58 indicates the left/right position in relation to the teeth together position (occlusion).

It will be appreciated that the multiplexer will transmit signals from its four inputs in sequence to its output 55. The output 55 of the multiplexer 54 is coupled to an analog to digital converter 60, where upon it is transmitted to a host computer 62. The host computer may comprise, for example, a conventional personal computer with a keyboard (not shown). The host computer 62 includes a CPU 63 and a preprocessor 65. The host computer 62 is also coupled to an adaptive interpreter 64, which in the preferred embodiment comprises a neural network. Both a printer 66 and a CRT display 68 are coupled to the host computer 62 for displaying the waveforms and diagnostic results as described in more detail below. It is preferred that all three components in the system 44 be optically coupled.

Figure 6B:
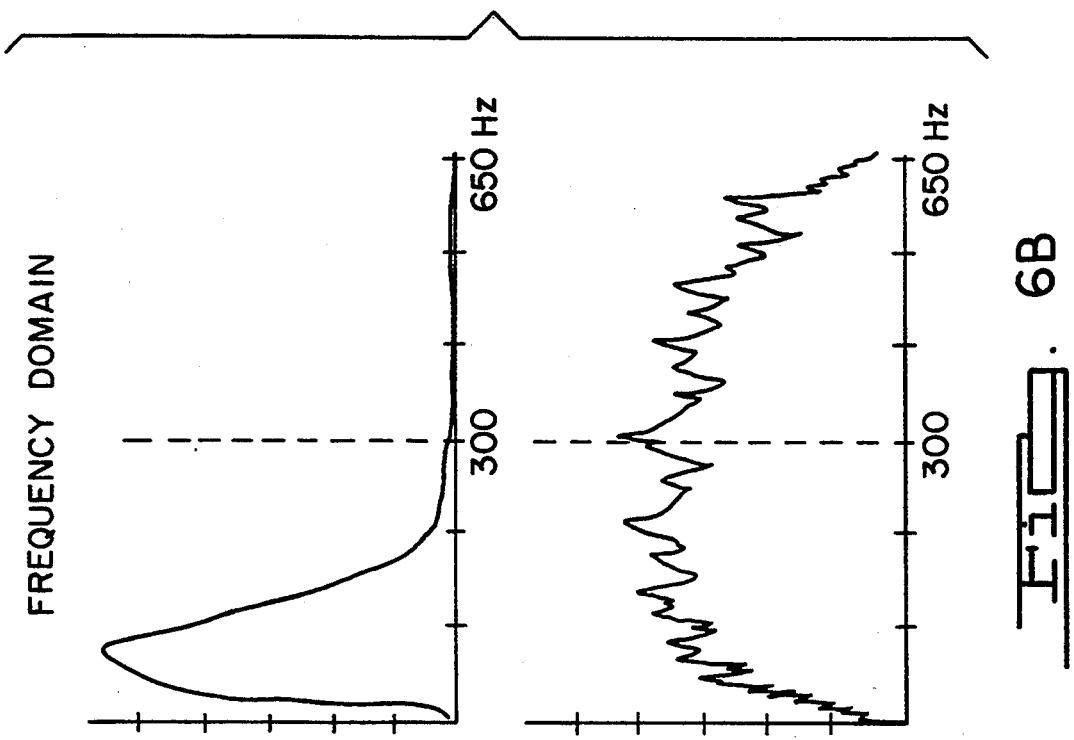
FIGS. 6A-B are diagrams of two types of TM joint vibrations.
Figure 6A:
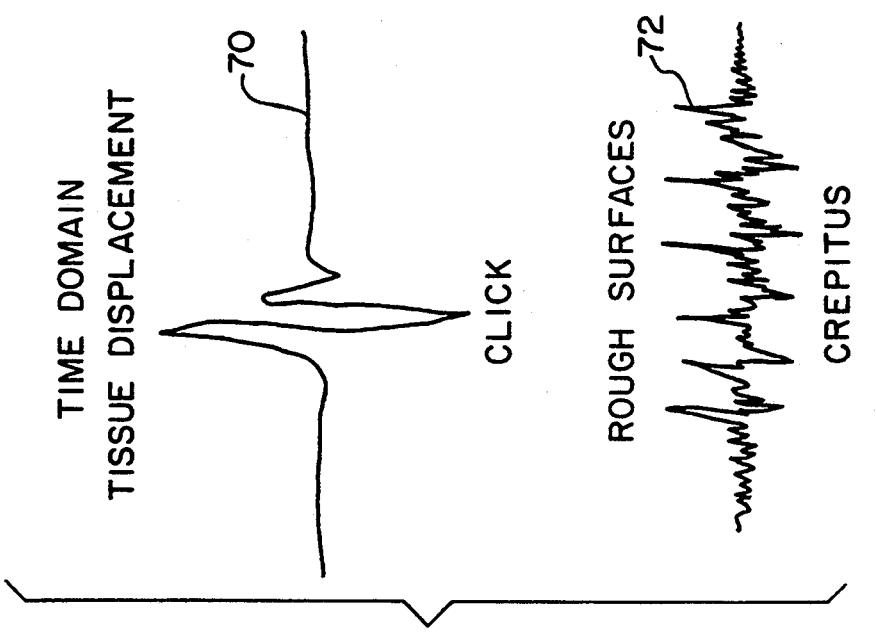

Referring now to FIGS. 6A and B there is shown comparison of two kinds of TM joint vibrations. The raw signal of a tissue displacement TM joint vibration 70 is shown consisting of relatively large amplitude, low frequency, vibrations. This kind of vibration is sometimes referred to as a "click". In contrast, a vibration caused by rough surfaces 72 is characterized by higher frequency and lower amplitude vibrations. This type of vibration is commonly referred to as "crepitus". In FIG. 6B these two kinds of TM joint vibrations are shown in the frequency domain. As expected, the tissue displacement vibration is comprises of primarily lower frequencies, while the rough surface vibration contains both lower and higher frequencies. This illustrates the importance of frequency analysis in characterizing TM joint vibrations.

Figure 7:
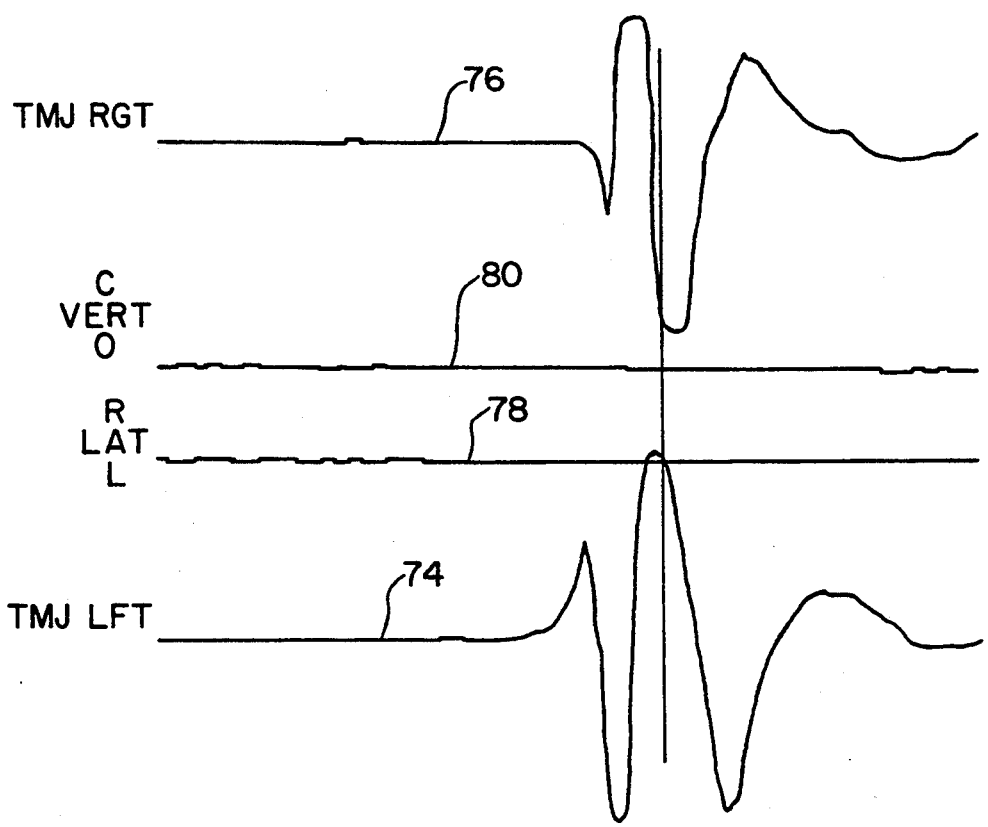
FIG. 7 depicts waveforms comparing left and right TM joint vibrations.

Referring now to FIG. 7, there is shown a display of the raw signal outputs from the left sensor 46 in curve 74 and of the right sensor 48 in curve 76. Also, the horizontal line 80 indicates the amount of opening of the jaw as measured by the jaw tracker 40 and the lower horizontal line 78 displays the left/right position of the anterior point of the jaw (relative to occlusion) as measured by the jaw tracker 40. It should be noted that when comparing the left and right vibration curves 74 and 76; the waveforms are very similar except that one is the mirror image of the other. Also, the left curve 74 begins slightly ahead of the right curve 76, but the left curve 74 moves up and the right curve 76 moves down.

These two curves reveal a phenomenon that occurs when there are left/right vibrations. Because the sensors are facing each other they are 180° out of phase, and, as the mandible vibrates left and right the same waveform is picked up on both sides except for the reversal in the phase. Also, the fact that one curve begins the vibration first and typically has a larger amplitude reveals that to be the side where the vibration is originating. The side opposite the originating side will have a signal that is a bit smaller and later in starting. This permits the differentiation of which side is originating the vibration. This is a very important consideration, particularly where treatment is called for. It is not unheard of for confusion to exist as to which side of the jaw is causing a particular vibration. This is a serious problem when corrective surgery is commenced on the wrong side. Thus, the vibration waveforms 74 and 76 contain information which allows the determination of which side is producing the vibration. This can be determined visually by the operator and signaled to the neural network by a single key press. Alternatively, it can be detected either in pre-processing or in the network.

Figure 8A:
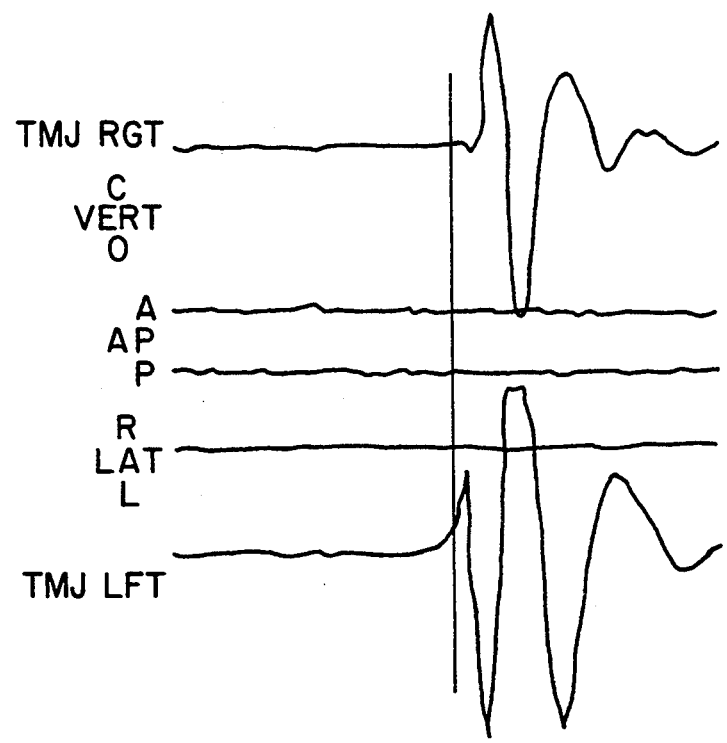
FIGS. 8A-D illustrate various types of vibration outputs produced by the joint diagnostic system of the present invention shown in FIG. 5.
Figure 8B:
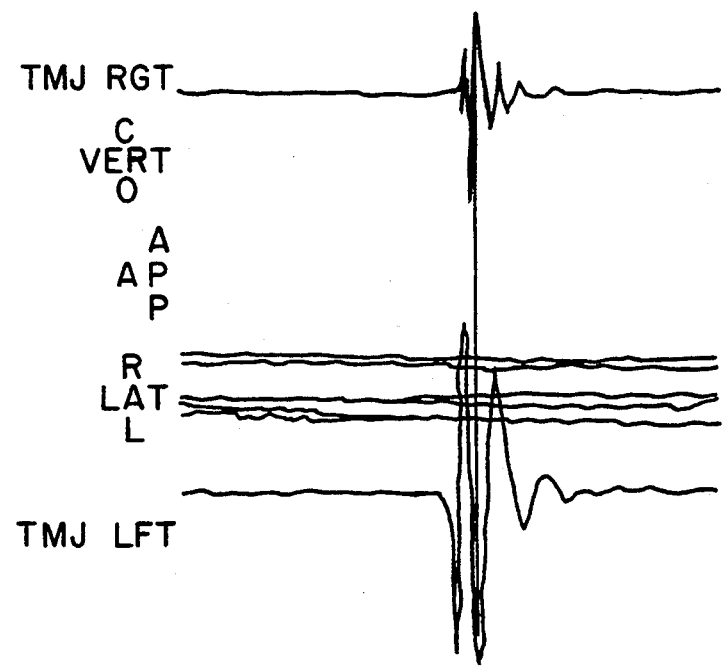
Figure 8C:
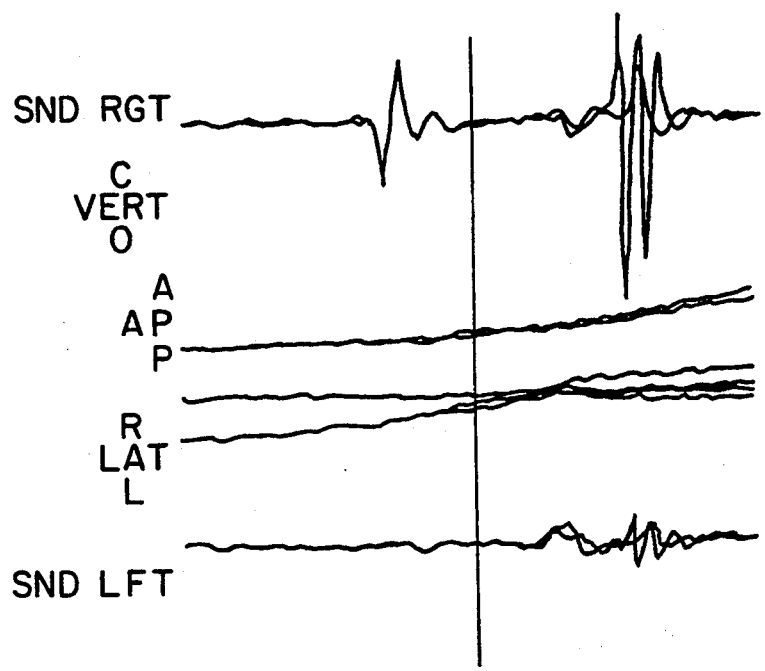
Figure 8D:
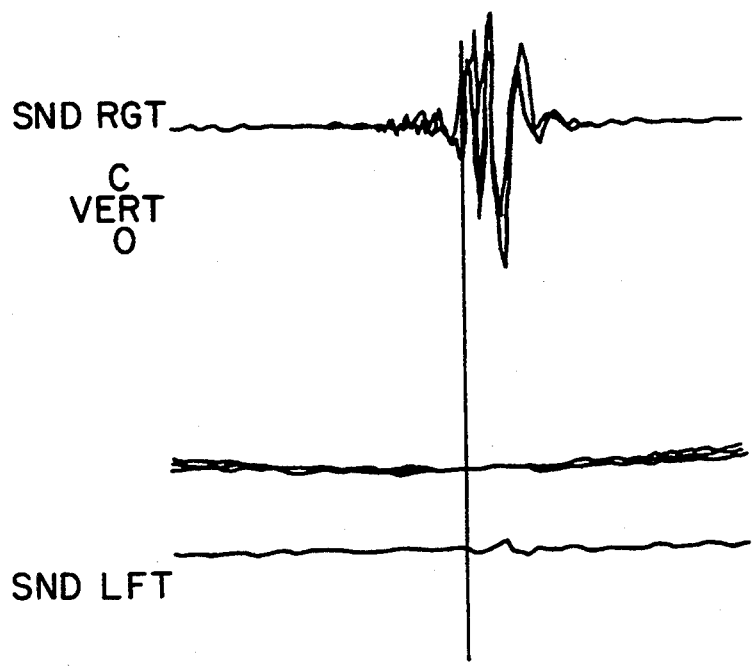

Referring now to FIG. 8A-D a variety of waveforms are shown. In FIG. 8A there is a waveform similar to the waveform shown in FIG. 7 where the lateral vibration in the opposing side is almost as large as that measured in the originating side. In FIG. 8B the amplitude in the opposing side is only about 50% of the amplitude in the originating side. In FIG. 8C the vibration in the opposing side is only a small percentage of the vibration being transmitted in the originating side. In FIG. 8D the vibration in the opposing side is virtually not existent. These figures illustrate a technique for differentiating the direction of the axis of the vibration within a joint. That is, where the axis of the vibration is orthogonal to the opposite TM joint there will be almost no vibration in the opposite side, as illustrated in FIG. 8D. Similarly, where the axis of vibration is in the direction of the opposite TM joint, there will be considerable conduction of vibration to the opposite joint as shown in FIG. 8A. This is another illustration of the wealth of information about the condition of the joint that is available from these vibration curves. This information can be visually detected by the operator and entered via the keyboard or detected in the pre-processing stage. A separate neural network could also be used to detect this.

Figure 9:
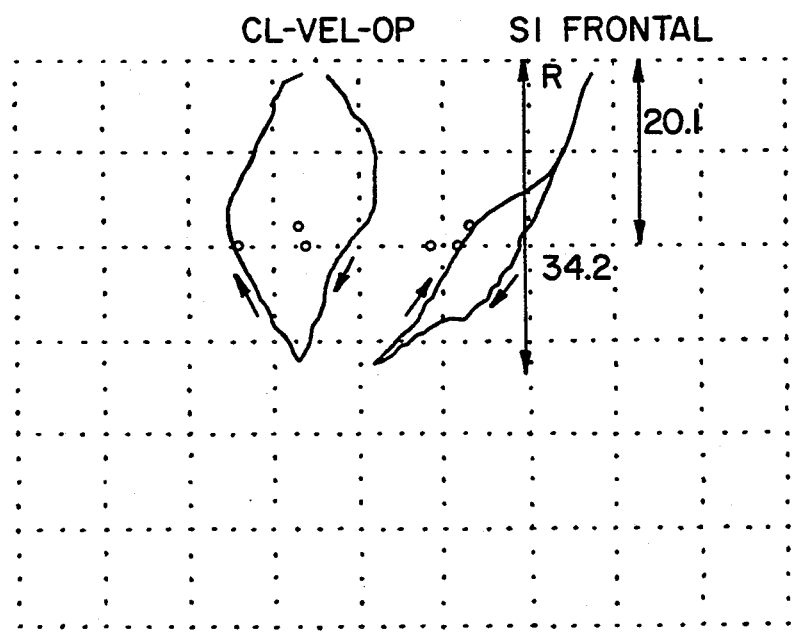
FIG. 9 is a diagram of the velocity and position of the jaw during measurement as recorded using the jaw tracker apparatus shown in FIG. 4.

Referring now to FIG. 9, there is shown an x, y positional display of information gathered from the jaw tracker 40. To the right of FIG. 9 is shown a display that is schematically representing viewing the patient from the front. Where the patient opens his jaw and deviates to the left (the patient's right). This indicates that the patient has a problem of lack of translation in the right joint, or restriction in translation in the right joint which causes the patient to deflect to the right on opening. The curve then proceeds in a clockwise direction back to the origin at the top right upon closing.

The curve in the left of FIG. 9 is a velocity profile. Again, the tracing is drawn on a clockwise manner with the opening velocity displayed on the horizontal axis and the vertical position displayed on the vertical axis. This curve reveals that when the patient opens his mouth wide, initially the mandible accelerates to some peak value at about 35% opening and then decelerates to 0 at maximum opening. Then, the mandible accelerates during closing up to about mid closure and then decelerates up to the point of tooth contact at the top of the curve. The small circles are displaying areas where a vibration is occurring. While the velocity curve may be used as a neural network input, in one embodiment the velocity and jaw position are estimated. This is accomplished by having the subject open and close his jaw in synchronization with a metronome (or a simulated metronome on the host computer screen). In this way the speed of opening and closing is standardized. The jaw tracker can be eliminated by using an estimated position based on the metronome cycle and range of motion (ROM) value.

Figure 10A:
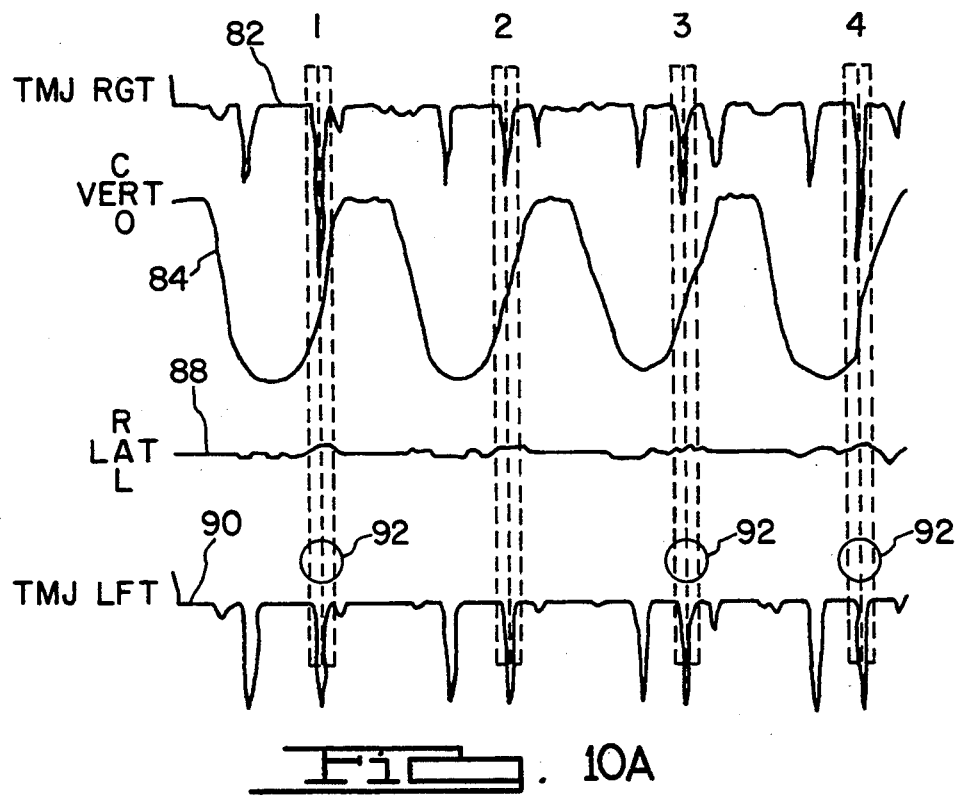
FIGS. 10A-C illustrate the display of vibrational patterns gathered during repeated opening and closings of a TM joint and also corresponding left and right frequency spectrums of the vibrations.
Figure 10B:
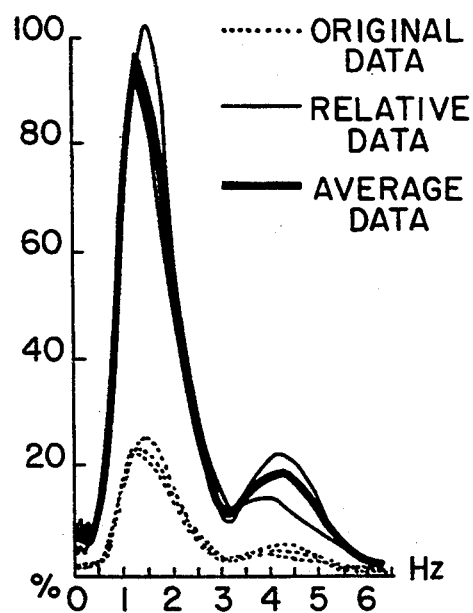

Referring now to FIG. 10A there is shown a raw display which includes the right TM joint vibration curve 82, the opening curve 84, the left/right position of the jaw 88 and the left joint vibration 90. In this display, the patient begins with their teeth together, opens wide and then closes and repeats this for four complete cycles of movement. In the process of analyzing the data, a window 92 is placed over a vibration. The window consists of the area between two dotted lines with a third dotted line defining the mid-point. A similar window is placed over each of the four vibration points in each of the four cycles. The windows 92 are centered on the onset of the vibration of interest. In this way, four samples of the same vibration are obtained. FIGS. 10B and C indicate the left and right frequency spectrums of these four vibrations respectively. By displaying both the average data and the relative original data, it can be seen how much the vibration is varying from cycle to cycle. In the preferred embodiment, there are 256 data points within each window.

Referring now to FIG. 11, there is shown a table of data resulting from analysis for the four vibrations in the four windows 92 shown in FIG. 10A. Because of variation between the data the four sets of data are averaged. In more detail, the data displayed in FIGS. 10B and C are determined by the preprocessor 63, using calculations including Fast Fourier Transforms. From the Fast Fourier Transforms various numeric values are calculated as displayed in FIG. 11. It will be appreciated that a Fast Fourier Transform is a well known mathematical method that breaks the vibration into its component frequencies. It is based on the principle that any signal can be described as the sum of the sine and cosine waves. The preprocessor 63 may comprise one of a number of conventional statistical analysis software products available such as MATLAB, available from The Math Works, Inc. of Natick, MA. The pre-processor 63 generates all of the desired statistical parameters. The peak frequency is the frequency that contributes the most power to the signal. The peak amplitude is the amplitude of the peak frequency. The median frequency is defined as the frequency at ½ of total power. The "Distance from C.O." is the distance in millimeters from centric occlusion to the onset of the vibration. "Slant Vert" indicates the distance from C.O. and "Lat" indicates lateral distance from C.O. Also shown in FIG. 11 is the integral parameter which is defined as the area under the original data curve of the FFT. Also, a reference frequency of 300 hertz is selected and the "integral" below 300 and above 300 hertz is defined, as well as the ratio of these two values.

It will be appreciated that all of the parameters in FIG. 11 are different ways of arriving at numerical indicators of how the energy is distributed in the vibration patterns. It is useful to arrive at such compressed descriptors of the waveform to use the data in accordance with the present invention. That is, it is desirable to limit the number of inputs to the neural network 64 used to analyze the patterns. Alternatively, the analysis of the raw signal would require 256 values for every window being analyzed.

In accordance with the present invention the inventors have found that certain parameters such as the median frequency, the integral, integral greater than and less than 300 hertz, and the greater than and less than 300 hertz ratio to be particularly useful in characterizing these joint vibration patterns. It is important to find which parameters are related to the various classifications of joint conditions and which are not. In this regard, it is one of the particular advantages of using a neural network in the system of the present invention that the neural network can inform the researcher of which parameters are useful and which are not. For example, peak frequency is a commonly fused parameter in previous attempts to analyze vibrational patterns from joints. However, once the neural network 64 had been trained in accordance with the techniques of the present invention, as described in more detail below, it was discovered that the parameter of peak frequency was not important to the classification. That is, the internal weights of the trained neural network associated with peak frequency were very low. Thus, while peak frequency is illustrated in the table in FIG. 11, as a parameter it is of limited usefulness, and satisfactory results may be obtained without using the peak frequency as input to the neural network. Thus the neural network used with the present invention becomes a research tool to assist in discovering the most important parameters for vibration characterization.

Figure 12:
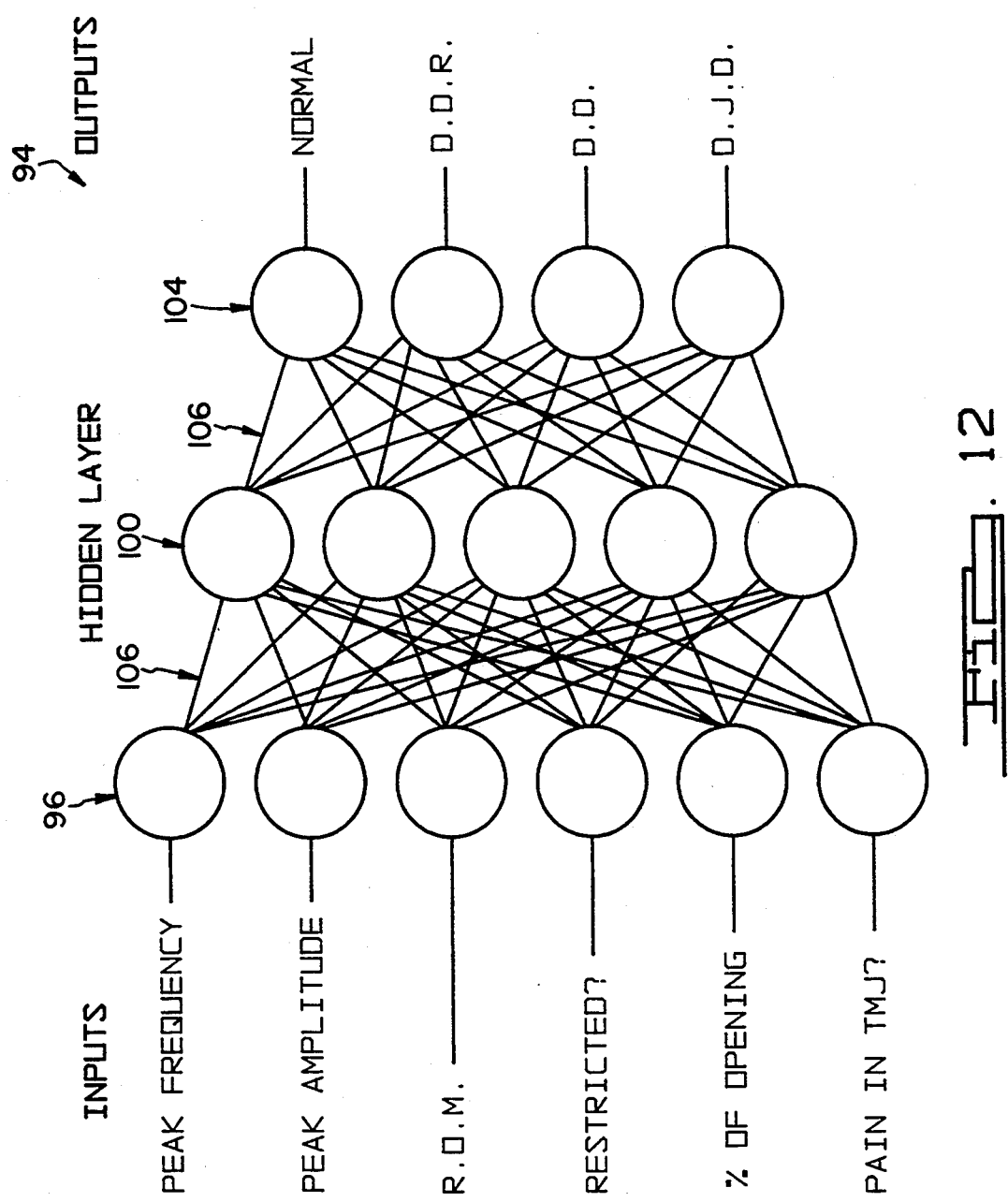
FIG. 12 is a diagram of one embodiment of the present invention employing a multi-layer perceptron adaptive interpreter used with the joint diagnostic system of the present invention shown in FIG. 5.

Referring now to FIG. 12 a schematic diagram of a conventional multilayered perceptron neural network 94 in accordance with the present invention is shown. It should be noted that the neural network 94 shown in FIG. 12 is illustrated schematically by function but may in practice comprise a neural network implemented in either hardware or software. For example, in the preferred embodiment, the neural network 64 utilized with the preferred embodiment of the present invention comprises a standard neural network software program known as Neuroshell sold by Ward Systems Group, Inc. of Frederick, Md.

In one embodiment of the present invention, the neural network 94 comprises a multilayer perceptron having six input nodes 96, a hidden layer having five neurons 100, and an output layer having four output neurons 104. Each of the neural network nodes 96, 100 and 104 are connected to nodes in an adjacent layer by means of adjustable synaptic weighted connections 106. In this embodiment, the inputs comprise "peak frequency", "peak amplitude" "range of motion" (ROM), "restricted?" (that is, whether the jaw opening is restricted or not) "percent of opening" (at time of vibration), and "pain in TMJ?". (Yes or No) These inputs are processed by the neural network in a conventional manner as described in more detail in R. P. Lippmann, "An Introduction To Computing With Neural Nets", *IEEE ASSP Magazine*, April, 1987, pp. 4–22, which is herein incorporated by reference. The neural network 94 is trained in accordance with conventional neural network training procedures.

In this application, however, it is critically important that the training data be properly selected. In the preferred embodiment, data from approximately 250 patients is used to train the neural network. These patients have conditions which have surgically and/or radiographically confirmed diagnoses. In the embodiment shown in FIG. 12 the neural network 94 is trained with patient data which have confirmed diagnoses that fall into one of four different categories: normal, displaced disc with reduction (DDR), displaced disc without reduction (DD) and degenerative joint disease (DJD). By way of example, assume that the first training data is from a subject having degenerative joint disease. The six parameters for that patient are input into the neural network 94 in the input nodes 96. These continuous valued and discrete inputs are processed by the neural network which generates some output level (e.g., a value between zero and one) at the four output nodes 104. Since the neural network has not yet been trained these outputs will generally be randomly distributed. Yet this patient has degenerative joint disease and it is desired that the neural network recognize the pattern of input parameters to indicate the classification of DJD. Thus, in accordance with a conventional neural network training techniques the internal weights connecting the input, hidden and output nodes are adjusted in a manner to increase the output for the DJD node and decrease the outputs for the other three nodes. In accordance with the preferred embodiment of the present invention the backpropagation procedure is used to train the network, as described in more detail in the above-discussed Littmann article. Each set of patient training data may typically require twenty to thirty thousand training iterations to achieve an acceptable level of performance.

It should be noted that the Neuroshell neural network product used in the preferred embodiment, allows the user to set up a training set and a test set at the same time. This permits the system to perform a self-test at various intervals, for example, at every one thousand iterations. The test set consists of a separate representative patient data set for which the answers (correct diagnosis) are known. The system then can check it's performance to determine whether it is yet producing the correct output response or whether it needs further training. Once the error rate has reached a minimum the training session is terminated for that patient data and it is determined that the neural network 94 is not overtrained. That is, training is stopped at the point of best generalization, before the training set is too well memorized.

Once trained, new patient data with an unknown condition can be taken, processed and input into the neural network. The output indicated by the output nodes 104 will each form a value between zero and one indicating how well the current patient's data matches classifications in the training set. It should be noted that this output is subject to an accuracy which can be measured by the performance on a new validation test set. Thus, if it is known that a particular classification is 95 percent reliable then the output is multiplied by 0.95 to give an indication of the probability of that answer being correct.

Figure 13:
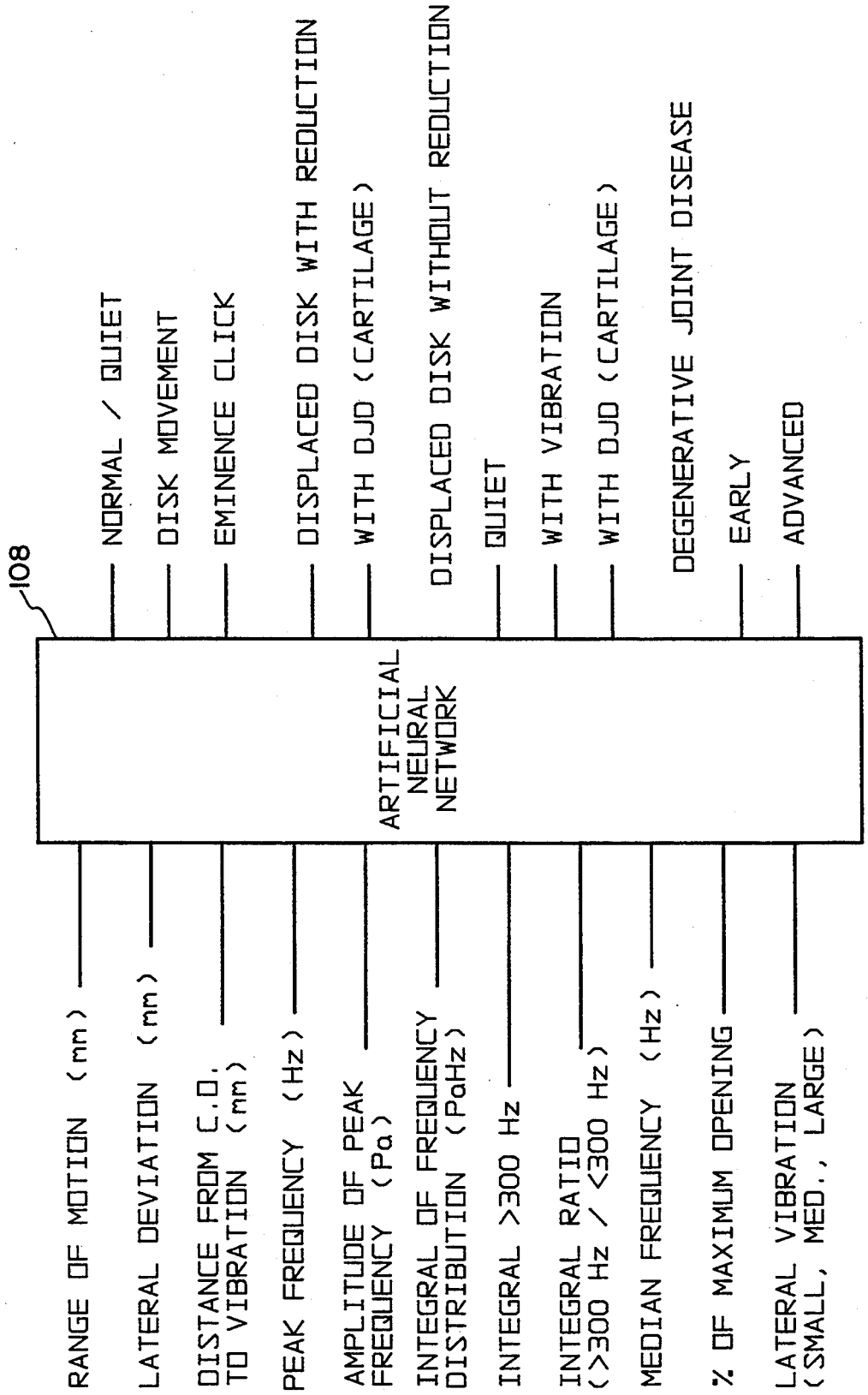
FIG. 13 is a schematic diagram of a neural network including inputs and outputs in accordance with a preferred embodiment of the present invention shown in FIG. 5.

Referring now to FIG. 13 another preferred embodiment of a neural network 108 used with the present invention is shown. The neural network is shown as a single box 108, for simplicity, however, it will be appreciated that it is essentially the same architecture as neural network 94 shown in FIG. 12 with additional input and output nodes. In this embodiment, the neural network 108 includes 11 inputs and 10 outputs. In this embodiment, the inputs "restricted" and "pain in TMJ" have been eliminated since training of the neural network on patient data has indicated that these are not important to the classification. That is, after training, low weights on weighted connections 106 are associated with those inputs. Restriction is a subjective yes/no (1 or 0) input. Lateral deviation is a continuous measure of left-right position of the jaw with respect to centric occlusion.

To explain the outputs in more detail, the classification "normal/quiet" describes a TM joint with a normal disk/condyle relationship (non-displaced) and a remarkably low amplitude of vibration across the measured frequency spectrum (20 to 650 Hz). The range of motion to wide opening is generally more than 40 mm (40 to 60 mm), the mandible does not deflect to one side at maximum opening more than 1–2 mm and the patient is able to move 10 mm or more in lateral excursion to the opposite side.

"Disk movement" describes a TM joint with a disk with either looseness in the joint capsule or a partial displacement and reduction. A moderate amplitude of low frequency vibrations (below 300 Hz), a normal range of motion (wide opening more than 40 mm) and a lateral excursion toward the opposite side (more than 10 mm) are present. Looseness most often occurs at or near mid-opening/mid-closing. A partial (incomplete) displacement with reduction or a small rotation of the disk can occur at any point.

"Eminence Click" describes a TM joint with a normal disk/condyle relationship (non-displacing) that exhibits a high amplitude, short duration, low frequency vibration (below 300 Hertz) at or near wide opening (frequently referred to as a "click" or "pop" by the patient). A normal range of motion in opening (more than 40 mm) and in lateral excursion to the opposite side (more than 10 mm) is seen. No indication of a "reciprocal" vibration is present and for motions between occlusion and 75% of maximum opening, no "click" occurs at all. This classification is most often confused with a reducing displaced disk (DDR) when the displacement occurs late in opening or early in closing.

"Disk displacement with reduction" (DDR) describes a TM joint with a disk that is displaced (anteriorly, medially, or antero-medially) with respect to the condyle, usually in the closed position. The disk subsequently reduces to a "normal relationship" during opening, and in doing so it causes a short duration, high amplitude, low frequency (below 300 Hz) vibration (clinically a "click" or "pop" is detected). A reciprocal vibration (at times palpable) often occurs at the point in closing where the disk displaces again. A normal range of opening and lateral excursion is present.. A late opening/early closing DDR may be confused with an Eminence Click.

"Displaced disk with reduction" (with degenerative joint disease (DJD)) describes a TM joint with a displaced disk (anteriorly, medially, etc.) that reduces to a "normal" relationship to the condyle, usually during opening. Considerable degenerative changes in the disk and the surrounding cartilage further compromise the TM joint's function. Short duration, high amplitude, low frequency vibrations are accompanied by simultaneous long duration, lower amplitude, high frequency vibrations. A normal range of motion, but with lateral deviations is typically recorded. This classification is most similar to Advanced DJD and could include a perforated disk (or posterior attachment).

"Displaced disk without reduction, quiet" ("closed lock") describes a TM joint with an acutely displaced disk (anteriorly, medially, etc.) and a restricted range of motion in opening and lateral excursion to the opposite side. Any vibration recorded has very low amplitude frequencies below 300 Hertz and represents continuous dislocation with respect to the condyle. If the condition is unilateral, a marked deflection towards the affected joint will occur during maximum opening, A condition that is often intermittent, "closed lock" may alternate with a displaced disk with reduction from one day/week to the next.

"Displaced disk without reduction (with vibration)" describes a TM joint with a displaced disk (anteriorly, medially, etc.) that does not reduce. Moderately restricted opening and lateral excursions to the opposite side coincide with low frequency vibrations of moderate amplitude. Disk movement with respect to the condyle is present (not reduction), but no high frequencies are seen that would suggest rough surfaces rubbing together during function. This classification is usually associated with long term displacement of the disk, but with successful adaptation rather than degeneration. This classification is most similar to "Disk Movement" (looseness in normal joint).

"Displaced disk without reduction (with DJD)" describes a disk that is displaced in relation to the condyle (anteriorly, medially, etc.) and does not reduce (chronic condition). Moderate amplitude vibrations appear all across the frequency spectrum (low to high), indicating rough surfaces within the joint rub against one another during function. The level of degeneration of the disk and associated cartilaginous tissue is measurable. Restriction of condylar translation may not be as noticeable as with Displaced Disk (with vibration), but the adaptation of the joint (to disk displacement) has been less successful. This classification is most similar to DJD (early).

The category "degenerative joint disease early" describes a TM joint with a primary clinical characteristic of a "crepitus" vibration of moderate amplitude all across the frequency spectrum (low to high). A normal or near normal range of motion is seen during opening and lateral excursion to the opposite side. The patient usually reports significantly impaired function and is not able to produce rapid, smooth movements of the mandible. If disc displacement exists it is permanent and no longer restricts condylar translation. This classification is most similar to disc displacement, without reduction with DJD.

The category "degenerative joint disease advanced" describes a TM joint with a greatly compromised function capability. The patient usually exhibits a normal or near normal range of motion in opening and lateral excursion to the opposite side. However, high amplitude, continuous vibrations, all across the frequency spectrum (low to high) are seen and the patient has difficulty in performing very simple functional tasks. This classification is an extension of DJD (mild/early to moderate) and would be more likely to include perforated discs and post-surgical cases (meniscectomy, etc.) where the degenerative process has not been halted.

Figure 10C:
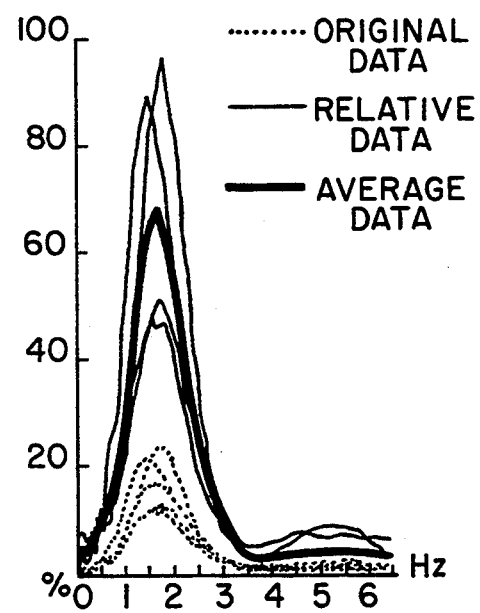

Referring now to FIG. 14, examples of output data from the neural network 108 are shown. In this example, which results from the table of input data shown in FIG. 11, and the curves in FIGS. 9 and 10, the left joint indicates a 0.36 output for the "normal with vibration" output and a 0.85 value for the "early degenerative joint disease" output. The 0.36 is a relatively low value indicating a low probability that that condition is the correct classification of the patient. It should be noted that in the preferred embodiment, only the top two choices are displayed so that the third choice would be lower than the second choice. In this case, the high probability of 0.85 is a relatively high probability for "early degenerative joint disease" indicating that to be likely the correct diagnosis.

It should be noted that the categories are not necessarily mutually exclusive. The "displaced disc with reduction" is of course mutually exclusive with respect to the "displaced disc without reduction" since you cannot have both a reduction and not have a reduction. Also, the "eminence click" is usually mutually exclusive with respect to the "displaced disc with reduction". A patient is not likely to have both of those at the same time. However, "degenerative joint disease" and "normal with vibration" are not mutually exclusive and it is possible that they are both present at the same time. For the right joint display in FIG. 14 it can be seen that a value of 0.23 is produced by the "displaced disc without reduction with vibration" output and a value of 0.95 for "advanced degenerative joint disease" indicating a high probability that that is the correct diagnosis.

It should be noted that one advantage of the use of neural networks in this application is that it does not force the system to produce a "correct" answer, or make a "best guess." Therefore, it is possible to have more than one high probability answer. This would be the case particularly where these two conditions may co-exist simultaneously. Also the condition may not fall exactly into any of the categories (but into the overlap of two categories) in which case by process of elimination one can eliminate many of the possibilities and the task of the clinician is to investigate the (two indicated) possibilities. Another possibility would be low numbers for all outputs which would indicate that the correct diagnosis is something other than those produced by the outputs. Thus, as described above, the vibrational patterns from a joint create a kind of fingerprint that is related to what is going on in the joint.

It should be noted that the neural network interpreters 64, 94, 108 and 136 used in the present invention are comprised in the preferred embodiment a multi-layer, feed-forward network trained with a backpropagation procedure. One advantage of this approach is that feed forward is a relatively fast single pass process. Also, since the neural network is non-linear it is able to solve complex problems which other types of processors have difficulty with. Since it is a supervised neural network it is trained with known data which permits the use of the wealth of data which is available regarding patient conditions.

Furthermore, the backpropagation training technique has been found to be well suited to the task of joint classification. It should be noted however that other types of neural networks may be successfully employed with the present invention.

Furthermore, the adaptive interpreter of the present invention may also comprise a non-neural network processor. For example, a fuzzy logic processor may also be used in certain situations. However, it should be noted that fuzzy logic is generally used when discrete, yes or no, type inputs are used. In the present invention typically the inputs are continuous valued inputs which are generally more suitable for neural networks than for fuzzy logic interpreters. However, there may be situations, such as where the inputs are discrete, where the fuzzy logic interpreter may be suitable. For further details of fuzzy logic interpreters see Kosko, B., "Fuzzy Systems as Universal Approximators", *Proc. of IEEE Fuzz-92*, March, 1992, and Kosko, B., *Neural Networks and Fuzzy Systems*, Prentice Hall, 1992, which are herein incorporated by reference.

An alternative to the neural network approach would be to use an expert system or rule based approach instead of a neural network or fuzzy logic interpreter. Generally, one problem with the rule based approach is that arbitrary threshold values must generally be established to decide, for example, that if a value is greater than "X" amount, it means one thing, and if it is less than that amount it means another. Since in the real world the transition is rather fuzzy, the rule based approach may not be the best to use. However, in certain situations it may be appropriate.

It should be noted that the sounds generated by displaced disks in the TM joint are relatively straightforward to diagnose. A displaced disk generally makes a relatively clearly diagnosable sound. One reason for this is the character of the TM joint which has an extreme amount of translation (forward and backward movement) during articulation. This high degree of translation is unique to the TM joint. Other joints generally only move in rotation during articulation. Because of this there has been much less success in diagnosing other conditions (such as degenerative joint disease) in the TM joint, since the sounds generated thereby are much more subtle and difficult to define. Likewise, there has been much less success in diagnosing conditions in the joints other than the TM joint. Other joints do not have the clearly distinguishable sounds of the displaced disk since they do not have disks, or the extreme translation as does the TM joint. Thus, common conditions such as degenerative joint disease in non-TM joints do not exhibit such easily recognizable sounds.

Further, many of these other joints, such as the knee and hip, are load bearing joints which are comprised of (load bearing) hyaline cartilage. In contrast, the TM joint is comprised (non-load bearing) fibrocartilage. There are a number of distinctions between hyaline cartilage and fibrocartilage. Hyaline cartilage has low vascularity and thus will not readily heal when torn. In contrast, fibrocartilage has higher vascularity, and will heal more readily when torn. Consequently, it is believed that these distinctions contribute to the qualitative differences between the vibrations emitted by the TM joint as opposed to load-bearing joints.

In any event, there has been very limited success in diagnosing non-TM joints using vibrations. The results to date appear to rely heavily on the experience and expertise of the individuals conducting the tests. Consequently, the previously applied techniques have not shown significant promise for wide clinical acceptance due to the subjective nature of the interpretation as well as the high level of skill required to interpret the results. To overcome these shortcomings, the joint diagnostic system of the present invention can be applied to degenerative joint disease and other conditions in non-TM joints, and in particular to load-bearing, hyaline cartilage joints.

Figure 15:
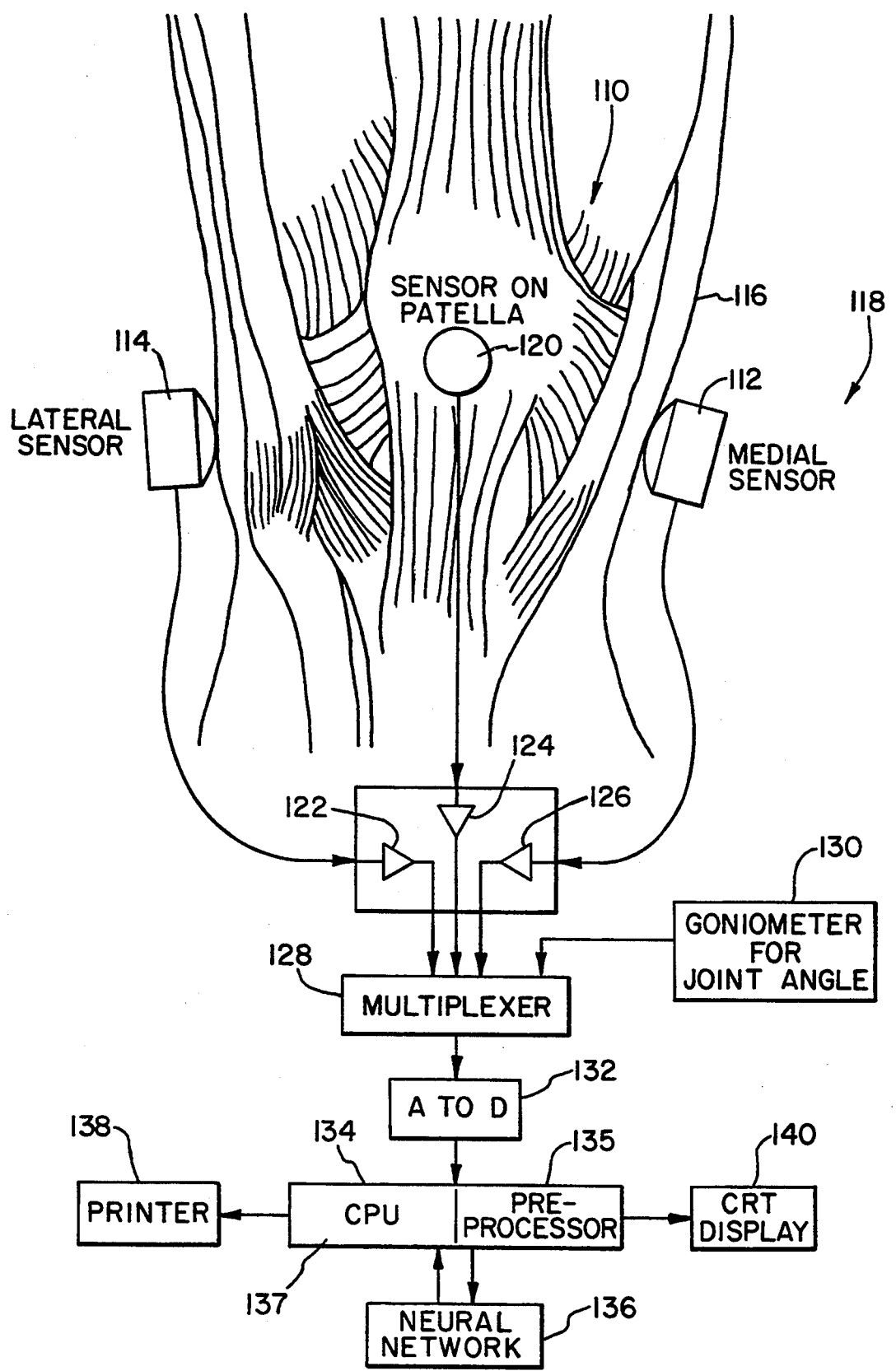
FIG. 15 is a knee joint diagnostic system in accordance with another embodiment of the present invention.

In accordance with a second embodiment of the present invention the diagnostic techniques are applied to the task of classifying vibrations from a knee joint. Referring now to FIG. 15 there is shown a knee joint 110 with medial 112 and lateral 114 sensors attached to the skin 116 immediately around the joint. In contrast to the diagnostic system 44 of the TM joint diagnostic system 54 shown in FIG. 5, the knee diagnostic system 118 in FIG. 15 includes a third sensor 120 positioned adjacent to the patella. The three sensors are connected to three amplifiers 122, 124 and 126 respectively, which are coupled to a multiplexer 128. A goniometer 130 is also connected to the multiplexer 128. It will be appreciated that a goniometer is a well known device which mechanically (or electrically) measures the angle between the bones connected to a joint. The multiplexer output is transmitted to an analog to digital converter 132 which transmits the signals from the sensors or from the goniometer to a host computer 134. A neural network 136 as described above is connected to the host computer 134. The host computer 134 includes a preprocessor 135 and a CPU 137. The output may be displayed either on a printed 138 or a CRT display 140.

Vibration signatures of specific conditions of the knee have been reported. See for example, McCoy, G. et al, "Vibration Arthrography As A Diagnostic Aid In Diseases Of The Knee", *J. of Bone and Joint Surgery*, Vol. 698, No. 2, March 1987, pp. 288–293 which is herein incorporated by reference. Signature parameters such as those reported in this study, in addition to above-discussed parameters (e.g., integral, integral ratio, median frequency, etc.) can be used in conjunction with the diagnostic system 118 of FIG. 15 to train the neural network 136 in a manner as discussed above in connection with diagnostic system 44.

It should be noted that once trained, the weights thereby derived can be inserted into other similar diagnostic systems to avoid repeating the training process. Particularly where the neural network is embodied in the hardware this will permit the use of simplified fixed weight neural network versions, which may then be mass-produced.

The diagnostic system of the present invention may be used to diagnose various kinds of joints and for a number of purposes. For example, in the field of knee diagnostics with respect to the tibiofemoral joint the following (and other) conditions might be diagnosed:
 a) general condition of articular cartilage and monitoring of degenerative or healing changes over time;
 b) meniscal lesions (tears);
 c) loose bodies;
 d) chondromalacia;
 e) arthritis;
 f) osteochondritis dissecans (a lesion of subchondral bone with localized necrosis);
 g) torn ligaments;
 h) verifying the efficacy of treatments such as abrasive chondroplasty.

With respect to the patella femoral joint the following are among the uses:
 a) chondromalacia;
 b) osteoarthritis;
 c) patella femoral malalignment and dynamic tracking problems;
 d) verifying efficacy of corrective procedures for tracking problems such as a lateral retinacular release.

In hip diagnostics the present invention can be used for the detection of hip abnormalities such as congenital dysplasia hip, which is not a degenerative joint disease. Also, it can be used for the detection and monitoring of degenerative joint disease such as arthritis or avascular necrosis. In the field of shoulder diagnostics it will be a useful diagnosis of arthritis. Also, by having the patient move his arm in a specific pattern it may be possible to detect rotor cuff tears and other lesions.

In the field of elbow, wrist and ankle diagnostics the present invention will be useful for general condition evaluation of articular cartilage and monitoring of degenerative or healing changes over time. In addition, it can be used for the detection of ligament damage. In the field of joint prostheses performance diagnostics, the present invention can be used for example: for the detection of "looseness" between implant components and the bone. In the hip this may include femoral stem component and acetabular cup. In the knee this may include femoral components, tibial components and patella components. In the shoulder this may include humeral, or glenoid components.

Quantitative analysis of the implant to bone interface may also be possible. This would include determining if the implant was anchored firmly by bony tissue or if it is bonded to the bone by a fibrous tissue; for the detection of disbonding between the bone cement and either the implant or surrounding bone; analysis of the tracking of implant components as they articulate against one another. This could include patella button tracking, patella clunk syndrome, engagement angle of posterior stability spike or femoral ball from acetabular socket dislocation; detection of knee or hip implant failure due to polyethylene wear resulting in metal to metal contact during articulation; and detection of disassociation or loosening of modular component assemblies such as polyethylene to acetabular cup interfaces and tibial polyethylene bearing to tibial tray interfaces and failure of associated locking mechanisms. These vibrations may be generated during articulation of the joint or when the patient's weight is applied and removed from the affected joint.

Also, the present invention may be used for diagnosing conditions (such as looseness, mechanical failure or detachment) of other implantable orthopedic devices such as fracture fixation devices. These may include, for example, bone plates, compression hip screws, intramedullary nails, etc. Since these devices may be used at non-joint locations, other movements besides joint movement may be necessary to cause them to generate vibrations. For example, the patient may load and unload the device (by applying weight to the affected bone) to cause the device to vibrate.

Other general uses for the present invention include the monitoring of the progression of any time varying condition of a joint. This progression may be a degeneration or perhaps a healing process. Also, the changes in a joint condition due to a controlled treatment program such as surgical correction procedures such as lateral retinacular release or tibiofemoral abrasionplasty, exercise or drug therapy could be monitored by periodic examination. The recordings of the joint vibrations could be analyzed and compared to detect trends.

From the foregoing it will be appreciated that the present invention provides a diagnostic tool for classifying joint conditions which is non-evasive, inexpensive, fast and easy to use. The joint diagnostic tool utilizes joint vibrations to arrive at a non-subjective joint disorder classification that is not dependent upon the skill of the person conducting the test. It can be utilized by persons without particular expertise in analyzing the joint vibrational patterns. Those skilled in the art can appreciate that other advantages can be obtained from the use of this invention and that modification may be made without departing from the true spirit of the invention after studying the specification, drawings and following claims.

What is claimed is:

1. A system for classifying degenerative joint disease conditions, the system comprising:
 a) sensor means for detecting a vibration pattern from the joint;
 b) preprocessor means for providing a predetermined set of data parameters descriptive of the vibration pattern; and
 c) trainable adaptive interpreter means for receiving said data parameters as input and producing an output which indicates at least one classification of the degenerative disease condition of said joint.

2. The system of claim 1, wherein said preprocessor means includes means for determining the frequency spectrum of said vibration pattern.

3. The system of claim 2, wherein said preprocessing means includes means for determining an integral of the frequency spectrum of said vibration pattern.

4. The system of claim 2, wherein said preprocessing means includes means for determining the median frequency of said vibration pattern.

5. The system of claim 1, further comprising means for measuring the instantaneous position of the joint during movement of the joint.

6. The system of claim 1, further comprising means for measuring the velocity of the joint during movement of the joint.

7. The system of claim 1, further comprising means for determining the range of motion of said joint, said range of motion being received by said interpreter as input.

8. The system of claim 1, wherein said interpreter comprises a neural network.

9. The system of claim 8, wherein said neural network is a multi-layer perceptron.

10. The system of claim 8, wherein said neural network contains adjustable weights which are generated during a training session using vibration patterns from joints with known conditions.

11. The system of claim 8, wherein said neural network contains fixed weights generated from a training session using vibration patterns from joints with known conditions.

12. A method for classifying degenerative joint disease conditions, said method comprising the steps of:
   a) detecting a first set of vibration patterns from one or more joints, the joints having a known condition;
   b) using said first set of vibration patterns and said known joint conditions to train an adaptive interpreter to produce an output indicating particular known degenerative joint disease conditions in response to particular vibration patterns;
   c) detecting a second set of vibration patterns from a subject joint; and
   d) transmitting said second set of vibration patterns to said adaptive interpreter wherein said adaptive interpreter generates an output indicating the presence of one or more of said known degenerative joint disease conditions in said subject joint.

13. The method of claim 12, wherein the step of using said first set of vibration patterns and said known joint conditions to train an adaptive interpreter further comprises the steps of interactively processing said first set of vibration patterns in a neural network until the output indicates the known joint condition.

14. The method of claim 13, wherein said step of interactively processing comprises a backpropagation training procedure.

15. The method of claim 12, wherein the joint comprises two portions on opposite sides of the joint and said step of detecting further comprises the step of placing one sensor adjacent to each joint portion.

16. The method of claim 12, further comprising the step of detecting the frequency spectrum of the vibration pattern.

17. The method of claim 16, further comprising the step of an integral of the frequency spectrum of the vibration pattern.

18. The method of claim 17, further comprising the step of the sampling only a portion of said detected vibration pattern, said portion beginning a period before and ending a period after said peak amplitude wherein only said sampled portion of first and second set of vibration patterns is transmitted to said interpreter.

19. The method of claim 18, further comprising the step of repeating the step of sampling a plurality of times and averaging said sampled vibration pattern before transmitting to the interpreter.

20. The method of claim 12, further comprising the step of measuring the instantaneous position of the joint during movement thereof.

21. The method of claim 12, further comprising the step of measuring the velocity of the joint during movement thereof.

22. The method of claim 12, wherein said adaptive interpreter is a neural network and wherein the step of using said first set of vibration patterns and said known joint conditions to train an adaptive interpreter includes the step of employing backpropagation to train the adaptive interpreter.

23. A system for classifying a trauma induced joint condition said system comprising:
   a) sensor means for detecting a vibration pattern from the joint;
   b) preprocessor means for providing a predetermined set of data parameters descriptive of the vibration pattern; and
   c) trainable adaptive interpreter means for receiving said data parameters as input and producing an output which indicates at least one classification of the trauma induced condition of said joint.

24. A system for classifying joint conditions in a load bearing joint, the system comprising:
   a) sensor means for detecting a vibration pattern from the joint;
   b) preprocessor means for providing a predetermined set of data parameters descriptive of the vibration pattern; and
   c) trainable adaptive interpreter means for receiving said data parameters as input and producing an output which indicates at least one classification of the condition of said joint.

25. The system of claim 24 wherein said joint condition is congenital.

26. The system of claim 24 wherein said joint is a knee.

27. The system of claim 24 wherein said joint is a hip.

28. A system for classifying degenerative joint disease conditions, the system comprising:
   a) sensor means of detecting a vibration pattern from the joint;
   b) means for receiving non-vibrational diagnostic information relating to said joint;
   c) preprocessor means for providing a predetermined set of data parameters descriptive of the vibration pattern and said diagnostic information; and
   d) trainable adaptive interpreter means for receiving said data parameters as input and producing an output which indicates at least one classification of the degenerative disease condition of said joint.

* * * * *

UNITED STATES PATENT AND TRADEMARK OFFICE
CERTIFICATE OF CORRECTION

PATENT NO. : 5,413,116
DATED : May 9, 1995
INVENTOR(S) : Radke et al.

It is certified that error appears in the above-identified patent and that said Letters Patent is hereby corrected as shown below:

ON THE TITLE PAGE, under Attorney, Agent, or Firm
"Harness, Dickey & Pierce" should be
--Harness, Dickey & Pierce, P.L.C.--.

Abstract, Line 10, "a" (first occurrence in patent and application should be --an--.

Column 2, Line 64, "Joint" should be --joint--.

Column 3, Line 47, "a-technique" should be --a technique--.

Column 6, Line 14, "comprises" should be --comprised--.

Column 8, Line 49, "fused" should be --used--.

Column 9, Line 59, "Littmann" should be --Lippmann--.

Column 10, Line 2, "it's" should be --its--.

Signed and Sealed this

Eleventh Day of August 1998

Attest:

BRUCE LEHMAN

*Attesting Officer*     *Commissioner of Patents and Trademarks*